United States Patent [19]

Childs

[11] 4,229,263

[45] Oct. 21, 1980

[54] RECOVERY OF METHYL HEPTAFLUOROBUTYRATE FROM METHANOL BY DISTILLATION

[75] Inventor: William V. Childs, Bartlesville, Okla.

[73] Assignee: Phillips Petroleum Company, Bartlesville, Okla.

[21] Appl. No.: 972,087

[22] Filed: Dec. 21, 1978

Related U.S. Application Data

[60] Division of Ser. No. 867,078, Jan. 5, 1978, Pat. No. 4,156,791, which is a continuation of Ser. No. 695,217, Jun. 11, 1976, abandoned.

[51] Int. Cl.$^2$ .................. B01D 3/36; C07C 69/62
[52] U.S. Cl. ........................ 203/44; 203/60; 203/66; 203/95; 203/98; 252/1; 252/182; 560/227
[58] Field of Search .............. 203/66, 50, 60, 39, 203/44, 95, 96, 97, 92, 93, 98, 99; 560/227; 252/182, 1

[56] References Cited

U.S. PATENT DOCUMENTS

| | | | |
|---|---|---|---|
| 2,662,914 | 12/1953 | Robeson | 562/509 |
| 2,666,797 | 1/1954 | Husted et al. | 568/842 |
| 2,683,721 | 2/1954 | Schlesinger | 260/343.3 R |
| 2,732,370 | 1/1956 | Codding | 526/247 |
| 2,775,633 | 12/1956 | Fenske et al. | 208/280 |
| 2,824,897 | 2/1958 | Wujciak et al. | 568/842 |
| 2,839,513 | 6/1958 | Ahlbrecht et al. | 526/246 |
| 2,858,331 | 10/1958 | Fenske et al. | 560/192 |
| 2,862,977 | 12/1958 | Schreyer | 568/842 |
| 2,922,816 | 1/1960 | Bruce | 260/544 F |
| 2,945,886 | 7/1960 | Brown | 260/570.9 |
| 2,951,871 | 9/1960 | Schroder | 260/462 R |
| 3,277,147 | 10/1966 | Maehleidt et al. | 560/125 |
| 3,321,284 | 5/1967 | Dunlop | 203/63 X |
| 3,390,191 | 6/1968 | Anello et al. | 568/842 |
| 3,663,629 | 5/1972 | Fischer | 568/842 |
| 3,959,389 | 5/1976 | Kurata et al. | 568/842 |

FOREIGN PATENT DOCUMENTS

| | | | |
|---|---|---|---|
| 994607 | 6/1965 | United Kingdom | 568/842 |
| 1213558 | 11/1970 | United Kingdom | 568/842 |

OTHER PUBLICATIONS

Technique of Organic Chemistry, vol. IV, Distillation, Weissberger, 2nd Ed., 1965, pp. 488–490.
Brown et al., 28 *J. Org. Chem.*, 3261-3263 (1963).
Foerst, *Newer Methods of Preparative Organic Chemistry*, vol. IV (1968), pp. 197 & 204–208.

*Primary Examiner*—Wilbur L. Bascomb, Jr.

[57] ABSTRACT

Esters are treated with alkali metal borohydride to produce alcohols. Substantially constant boiling admixtures of: methanol/methyl heptafluorobutyrate, water/1,1-dihydroheptafluorobutanol, and water/methyl heptafluorobutyrate are described.

5 Claims, No Drawings

RECOVERY OF METHYL HEPTAFLUOROBUTYRATE FROM METHANOL BY DISTILLATION

This is a Divisional Application of Ser. No. 867,078, filed Jan. 5, 1978; and now U.S. Pat. No. 4,156,791, patented May 29, 1979 which is a Continuation of Ser. No. 695,217, filed June 11, 1976, now abandoned.

FIELD OF THE INVENTION

The invention relates to the production of alcohols. In other aspects of the invention, the invention relates to substantially constant boiling compositions of matter.

BACKGROUND OF THE INVENTION

Various alcohols, including fluorine-containing alcohols, have been prepared in the past by the reduction of their corresponding acid or ester precursors with an alkali metal borohydride with varying degrees of success. In particular, yields of fluoroalcohols from such methods have been relatively low, and the recovery of products has been generally difficult or inconvenient. Typically, a prior art process prepares 1H,1H-heptafluorobutanol by a reductive process while employing relatively massive amounts of diluent, followed by multiple evaporation and solvent extraction steps to recover these products.

BRIEF SUMMARY OF THE INVENTION

I have discovered methods of producing alcohols by reductive treatment of an ester with an alkali metal borohydride, while yet obtaining good yields, and my process is susceptible to effective separation procedures. In my studies, in the production of such alcohols, I have also discovered certain novel azeotropes. I also discovered certain separation procedures to recover the alcohols produced by my process.

DETAILED DESCRIPTION OF THE INVENTION

In an aspect of my invention and process, esters are reduced with alkali metal borohydrides employing a proton source which is an alcohol, and in some aspects alternatively can be water.

Esters

The ester compounds used in my process can be represented by R—(COOR$^1$)$_a$ in which a is an integer and is 1 or 2. R is an alkyl or alkylene radical or fluorine-substituted alkyl or alkylene radical of 1 to 10 carbon atoms per radical. R$^1$ is an alkyl or fluorinated alkyl radical of 1 to 8 carbon atoms per R$^1$ group, more usually for convenience 1 to 3 carbon atoms per group and preferably is alkyl.

Typical examples of these esters include isopropyl trifluoroacetate, sec-butyl pentafluoropropionate, methyl heptafluorobutyrate, dimethyl perfluorosuccinate, dipropyl perfluoroadipate, dimethyl perfluorosebacate, octyl perfluoro-3-methylbutyrate, methyl perfluoro-3,4-dimethylpentanoate, 2-ethylhexyl perfluorohexanoate, ethyl perfluorooctanoate, methyl perfluorodecanoate, 2,2-difluoroethyltrifluoroacetate, 1,1-dihydroheptafluorobutyl heptafluorobutyrate, isopropyl acetate, methyl acetate, methyl 2-fluoroacetate, 2ethylhexyl heptanoate, and the like, and mixtures thereof.

Esters wherein R is fluorinated typically include isopropyl trifluoroacetate, sec-butyl pentafluoropropionate, methyl heptafluorobutyrate, dimethyl perfluorosuccinate, dipropyl perfluoroadipate, dimethyl perfluorosebacate, octyl perfluoro-3-methylbutyrate, methyl perfluoro-3,4-dimethylpentanoate, 2-ethylhexyl perfluorohexanoate, ethyl perfluorooctanoate, methyl perfluorodecanoate, 2,2-difluoroethyl trifluoroacetate, 1,1-dihydroheptafluorobutyl heptafluorobutyrate, and the like, and mixtures thereof.

Presently preferred are the monoesters which can be represented by the formula R—COOR$^1$, particularly the methyl esters of perfluoro monocarboxylic acids. However, esters such as 1,1-dihydroperfluoroalkyl perfluoroalkanoates also can be used advantageously, since in these instances one molecule of such ester can be converted by my reductive treatment with an alkali metal borohydride to result in two molecules of the desired 1,1-dihydroperfluoro aliphatic alcohol.

Reducing Agents

The reducing agents employed for reducing the ester to the corresponding alcohol are the alkali metal borohydrides. These can be employed in a finely divided form or as pellets. These borohydrides typically include sodium borohydride, potassium borohydride, lithium borohydride, rubidium borohydride, as well as cesium borohydride, any of these alone or in admixture. The sodium and potassium borohydrides presently are preferred for availability and cost factors. The sodium borohydride presently is particularly convenient because of its effectiveness and its ready availability.

Proton Source

The third reactant in the treatment process is a proton source compound which is a free alkanol, or in certain instances can be water. The alkanol can be represented by the formula R$^1$OH wherein R$^1$ is as previously described.

Exemplary alkanols include methanol, ethanol, isopropanol, 2,2,2-trifluoroethanol, sec-butanol, 4-methylbutanol, 2-ethylhexanol, 1,1-dihydroheptafluorobutanol, and the like, and mixtures thereof. Of these, the lower alkanols having 1–3 carbon atoms per molecule are preferred, and methanol is particularly convenient because of its ready availability and low cost. Although other alkanols can be used, they appear to offer no particular overall advantage in effectiveness and convenience over the lower alkanols. If desired, the free alkanol can be the same as the proton donor alcohol which is a product alcohol of a given reduction reaction, such as 1,1-dihydroperfluoroalkanol.

In my invention the proton source preferably is the alkanol. Of course, in those embodiments in which water is appropriate, mixtures of water and any of the alkanols can be employed where desired in proportion. Presently preferred is, when such an admixture is employed, an admixture wherein the alkanol predominates by weight.

Reaction Conditions

The reaction conditions under which the ester, the alkali metal borohydride, and the proton source are employed, in general can be any suitable conditions of temperature, pressure, and time sufficient to promote substantial reduction of the ester compound. The temperature should be temperature effective to provide a suitable reaction time and an exemplary temperature range is considered to be from about 0° C. to 150° C., presently preferably about 20° C. to 100° C. The reaction time can vary widely, depending upon temperature, as well as specific reactants, but exemplary times can be expected to be generally in the range of about 0.1 to 20 hours. Pressures can be as convenient, and atmospheric pressure is suitable and convenient. However, the pressure can vary from such as about 10 to 100 psia (68.9–689 kPa). The reaction procedure generally can be carried out either batchwise or continuously as the practitioner may prefer.

Method of Contact of Ester and Borohydride

A preferred mode of contact which makes efficient usage of the alkali metal borohydride to yield a reaction product containing increased amounts of desired product alcohol, and which is particularly convenient when employing a batchwise process, is (I) to prepare a stirred mixture of alkali metal borohydride, powder or pellets, in undiluted ester, to which admixture then slowly is added the proton source compound. This can be termed the "neat ester" mode. The proton source material, alkanol or water, should be added at a rate substantially equivalent to the rate at which it is being reacted. It is convenient and effective to slowly add the proton source material to a refluxing mixture of the slurry of ester/alkali metal borohydride. In many instances, this particular process/contact mode produces virtually twice as much product alcohol, per weight unit of borohydride employed, as any other process mode. This mode of contact is effective and advantageous for both fluorine-containing and non-fluorinated esters.

The next most preferred mode of contact, in accordance with my invention, and which also is productive though usually not quite as productive as the mode described hereinabove, is (II) to make an admixture of the ester and the proton source, preferably an alkanol, which mixture then is slowly added to the solid undispersed alkali metal borohydride at a rate substantially equivalent to the rate of reaction. This mode, which can be termed the "diluted ester" mode, is particularly advantageous for the reduction of the esters of perfluorinated acids. In this mode, alcohols of the formula $R_f$-$(CH_2OH)_a$ preferably are prepared by employing an ester of the formula $R_f$-$(COOR^1)_a$ wherein $R_f$ is a $C_1$-$C_{10}$, more usually $C_1$-$C_8$, perfluoro alkyl or alkylene radical. This mode of contact, while generally somewhat less productive than the method described hereinabove, nevertheless is far more productive and more effective than the mode described in such as British Pat. No. 1,213,558 wherein an ester is slowly added to a solution of sodium borohydride and ethanol, which British mode produces far less product per unit of alkali metal borohydride than does the mode of contact of my invention.

My invention produces desired product alcohols in good yield with good utilization of alkali metal borohydrides. Although I do not wish to be bound by a theoretical explanation when I have described effective and patentable procedures, nevertheless it may be that the presence of suitable amounts of a specified proton source, coupled with specified modes of contact, provide a favorable environment for desired reactions. It may possibly be explained by theorizing better control of proton availability, possibly formation of intermediate complexes between the boron and alkoxyl groups. In the preferred contacting mode wherein I get such high yields of alcohol product, it appeared that one mole of alkali metal borohydride can reduce about 2 moles of ester group. In this aspect, it would appear that about half the required amount of hydrogen can be supplied by the hydride, with the balance coming from the proton source. Small amounts of molecular hydrogen can be formed, possibly in a competing reaction, and may be evolved from the system.

In the reaction itself, while the ratios of proton source to ester can vary widely, I presently consider exemplary a range of about 1:1 to 2.5:1, preferably about 1.7:1 to 2.2:1, moles of proton source, alcohol or water or both, per mole of ester group present -(-COOR$^1$). These amounts of alcohol apply whichever mode of contact is employed.

The amount of alkali metal borohydride employed can also vary widely, as long as sufficient is provided to effectuate the reaction desired. Depending on the mode of contact a recommended range is about 0.1:1 to about 1.5:1 moles of alkali metal borohydride:mole of -(-COOR$^1$) group present. When employing the premode of contact wherein a suitable mixture of ester and free alkanol proton source is slowly added to undispersed reducing agent, the amount of alkali metal borohydride initially present will generally be in the range of from about 0.9:1 to 1.5:1, preferably 1.0:1 to 1.2:1 moles of alkali metal borohydride per mole of -(-COOR$^1$) group present. When employing the preferred mode of contact (I) wherein undiluted alkanol or water proton source is slowly added to a stirred mixture of the reducing agent in undiluted ester, the amount of alkali metal borohydride initially present will generally be in the range of 0.3:1 to about 0.8:1, preferably 0.5:1 to about 0.6:1, moles of alkali metal borohydride per mole of -(-COOR$^1$) group present.

Recovery of Product Alcohol

Upon completion of the reductive reaction, the reaction admixture from reduction can be separated and the desired product alcohol isolated using any suitable procedure, such as fractional distillation, solvent extraction, filtration, and the like. My process results in product alcohols which can be represented by the formula R-$(CH_2OH)_a$ wherein a and R each are as described previously. In a preferred aspect employing my contacting mode II, the resulting alcohols can be represented by $R_f$-$(CH_2OH)_a$, wherein $R_f$ is a $C_1$-$C_{10}$ perfluoro alkyl or alkylene radical.

Ester Precursor

In another aspect of my invention, a carboxylic acid as ester precursor can be employed. The carboxylic acid can be represented by R-$(COOH)_a$. In this aspect, the ester precursor, the carboxylic acid R-$(COOH)_a$, is contacted with an alkanol R$^1$OH under esterification conditions effective to produce a reaction mixture containing ester compounds of the formula R-$(COOR^1)_a$.

In this method wherein I start with an ester precursor, the desired acid and desired alkanol are esterified at temperatures which can range widely, typically in a range of such as about 0° C. to 150° C., using reaction times suitable for the esterification desired, such as about 0.1 to 70 hours, and at pressures suitable and convenient, preferably such as to maintain substantially liquid phase in the reaction admixture. If desired, an esterification catalyst can be employed to promote the reaction. For esterification, the ratio of R$^1$OH alkanol to the acid compound generally will be in the range of about 2.5:1 to about 10:1, presently preferably about 3:1 to 5:1 mols of R$^1$OH per mole of acid group —(COOH)$_a$ group present. If desired, greater amounts of the alkanol can be employed since such tend to help to speed the esterification reaction.

The resulting esterification admixture then can be separated, such as by distillation, to recover unconverted alkanol which can be recycled to the esterification step, and to recover substantially pure ester and residual proton source alkanol, or a suitably already mixed stream of both the alkanol R$^1$OH and ester, for use in the reductive step with the alkaliborohydride.

The so-produced ester compound, together with necessary quantities of the alkanol, are contacted with and reacted with the alkali metal borohydride as described herein previously under conditions effective to produce a reaction mixture containing the product alcohol. This can be carried out by making the suitable mixture of ester and alkanol and slowly adding this to solid undispersed alkali metal borohydride. Alternatively, and the particularly preferred mode at present, is to make a stirred mixture of alkali metal borohydride, powder or pellets in the undiluted ester compound itself, and then slowly add the alkanol or water or both as proton source to the stirred mixture.

The product alcohol-containing-reaction mixture then is subjected to a separation procedure to isolate and recover the R—(CH$_2$OH)$_a$ product alcohol. The recovered R$^1$OH alkanol, which includes the liberated esterification alkanol as well as any residual proton source alkanol, can then be recycled to the esterification zone.

In a specific embodiment as exemplary of the use of an acid precursor, methanol and heptafluorobutyric acid are fed individually to reaction means under suitable conditions of time, temperature, and pressure, as described above, to result in an admixture containing methyl heptafluorobutyrate. The resulting reaction admixture effluent from such esterification can be conducted to separation means, such as fractionators, absorbers, and the like, to separate the esterification reaction admixture into desired components streams. Typically, in the formation of methyl heptafluorobutyrate, distillation is a convenient method of separation.

In the specific embodiment herein described employing methanol and heptafluorobutyric acid as reactants, distillation of the resulting esterification reaction admixture results in a methanol/methyl heptafluorobutyrate azeotrope characterized by a boiling point of about 56–58° C. at substantially atmospheric pressure. This azeotrope also is characterized by about 78–80 weight percent methyl heptafluorobutyrate and correspondingly about 22–20 weight percent methanol. It is noted that the specific azeotrope of my discovery is a minimum boiling azeotrope boiling at a temperature substantially below both the boiling point of methanol, 65° C., and of methyl heptafluorobutyrate, 80° C.

Particularly advantageous is the direct employment of the methanol/-methyl heptafluorobutyrate azeotrope as a mixture to the borohydride in accordance with the diluted ester aspect of the reductive process described hereinabove. The methanol provides the proton source needs, and the ester itself is reduced by the reductive treatment with the borohydride. This azeotrope can be supplemented with additional methanol or other proton source, if desired, in the reductive treatment.

In the particular aspect employing the methanol/-methyl heptafluorobutyrate azeotrope in reduction of the methyl heptafluorobutyrate, reductive treatment of this azeotrope with alkali metal borohydride results in a reaction mixture containing very substantial amounts of 1,1-dihydroheptafluorobutanol. It has been found by me that the ultimate yield of alchohol produced when employing this azeotrope is unusually high. Thus, from my experience, such as about 5 kilograms of this product alcohol can be obtained per kilogram of sodium borohydride. Uniquely, it appears that this azeotropic admixture, besides being convenient to prepare and incidental in the preparation of the methyl heptafluorobutyrate as described above, contains apparently close to optimum porportions of methanol:ester for efficient conversion of the ester to the desired end product alcohol.

Treatment of the Reduced Admixture

After the reductive treatment of the ester with the borohydride as described hereinabove, the resulting reduced admixture then can be treated to recover the product alcohol.

The reduced admixture containing unreacted ester, unconverted borohydride, product alcohol, proton source if different from product alcohol, various borates, and the like, advantageously can be acidified with aqueous mineral acid, and the resulting acidified admixture then can be distilled to recover alkanol R$^1$OH, water, and product alcohol R—(CH$_2$OH)$_a$.

The treatment with acid destroys any unconverted alkali metal borohydride which may be present, converts various borates to boric acid, and in general quenches the reaction and facilitates recovery of the product. For this purpose, any strong mineral acid can be employed, employing concentrations such as in the range of about 1 to 50 weight percent. An aqueous solution of the relatively nonvolatile acid sulfuric acid at a concentration of such as about 5–35 weight percent, presently is preferred. The aqueous acid can be added as rapidly as the reaction will permit, since some gases and/or heat may be evolved, and at any convenient temperature within the temperature range for the reduction reaction itself. Room temperature is convenient and can be maintained by suitable cooling means for a necessary period. The total amount of acid can vary widely, so long as a sufficient amount of acid is employed to accomplish the desired function. The amount exemplarily can range from about 1 to 2 acid equivalents per mole of hydride originally employed in the reduction reaction.

The resulting crude acidified reduction admixture then can be separated by various procedures as may be necessary, including fractionation, extraction, crystallization, absorption, and the like, as well as various combinations depending on the particular reactions employed or desired by those skilled in the art. As exemplary, when 1,1-dihydroheptafluorobutanol is the product alcohol, a preliminary flash distillation can be employed to remove the 1,1-dihydroheptafluorobutanol as its water azeotrope from the bulk of the water and from inorganic by-products. Such flash distillation provides a mixture of product alcohol along with usually substantial amounts of residual proton source alkanol liberated esterifying alkanol, and water. The resulting mixture then can be separated by such as fractional distillation to isolate and recover the product alcohol.

Separated proton source, alkanol, and water, where desired, can be recycled to the reductive step, or to the esterification step, as may be desired. Preferably and conveniently the proton source alkanol and esterifying alkanol are the same.

In a preferred embodiment, the esterifying alkanol typically and preferably is a $C_1$–$C_3$ alkanol such as methanol, and a fluoroacid, typically and preferably a perfluoro monoalkanoic acid such as heptafluorobutyric acid are reacted in an esterification zone. The resultant esterification admixture is separated, and the ester fed to the reduction zone along with free alkanol as proton source. The free alkanol preferably and conveniently is the same alkanol as employed in the esterification step. The alkali metal borohydride such as sodium borohydride is fed into the reduction zone. After reduction, an aqueous acid, such as sulfuric acid, is added to the reduction zone to quench the reaction. The quenched product mixture is separated to recover the alcohol compound of the formula $R_f$—$CH_2OH$ wherein $R_f$ is a $C_1$–$C_8$ perfluoroalkyl radical, such as 1,1-dihydroheptafluorobutanol.

A feature of this combination process is that the $R^1OH$ reagent, e.g. methanol, is used in every stage. No other extraneous diluent or solvent, other than water in the aqueous acid, need be introduced into the system.

Alternatively, employing the esterification mode as first step, wherein an ester of the formula $R+(COOR^1)_n$ is first formed, the resulting esterification admixture can be separated, such as by distillation to recover unconverted esterifying alkanol $R^1OH$ for recycle to the esterification step, and to recover substantially pure ester. In this application of the "neat ester" mode, a slurry then is formed of the alkali metal borohydride in the undiluted ester, and to this then is slowly added an effective quantity of proton source alkanol to result in the reduction reaction admixture containing the product alcohol, as hereinbefore described.

The resulting reduction admixture then can be acidified with aqueous acid as described, and treated as hereinbefore described. The residual $R^1OH$ proton source as well as the newly liberated esterification $R^1OH$ alkanol can be recycled to the esterification step, if desired.

In a preferred exemplification of this embodiment, the proton source is a $C_1$–$C_3$ alkanol such as methanol, the acid compound is a RCOOH compound wherein R is a perfluorinated $C_1$–$C_8$ alkyl radical, such as heptafluorobutyric acid, the alkali metal borohydride is sodium borohydride, the aqueous acid is aqueous sulfuric acid, and the product of the reaction is a product alcohol having the formula R—$CH_2OH$ wherein R is a $C_1$–$C_8$ perfluorinated alkyl radical, such as 1,1-dihydroheptafluorobutanol.

In a modification of the acidification recovery procedure, the reduction admixture resulting from reaction of the ester, borohydride, and proton source can be treated with aqueous mineral acid as described above. The acidified reduction admixture then is distilled to produce a distillate comprising major amounts of proton source alkanol esterifying alkanol, water, product alcohol, and minor amounts of boron-containing by-products which will normally include borate esters of the desired product alcohol. This step can be accomplished by simple distillation or by a flash distillation to separate the bulk of the organic reaction mixture from the bulk of the water and inorganic reaction by-products. Whatever procedure is employed, at least minor amounts of borate esters generally are codistilled with the product in this step.

Thereafter, the resulting distillate is subjected to fractional distillation to isolate and recover desired product alcohol. Since water is present, at least one intermediate distilative cut comprising a water-wet product alcohol also can be recovered. Thus distillate streams of this fractional distillation include a stream of desired product alcohol, a stream of water-saturated product alcohol, and leaving a high boiling distillative bottoms product comprising borate esters of the product alcohol.

In accordance with one aspect of this separation, the residual distillative bottoms thereafter can be contacted with the water-wet product alcohol cut, employing any suitable conditions of time, temperature, and pressure effective to hydrolyze the borate esters in the kettle bottoms. If desired, assistance can be supplied by acidifying kettle bottoms with a small amount of mineral acid. In general, such hydrolysis occurs at temperatures in the range of about 20° to 100° C. for a suitable time such as 0.1 to 20 hours. As hydrolysis of the bottoms proceeds, boric acid is precipitated, and the organic phase becomes enriched in desired product alcohol. Boric acid can be removed easily by such as filtration. The filtrate then can be treated for recovery of the product alcohol, such as by recycling of the filtrate to the fractional distillation step.

Alternatively, rather than contacting the residual distillative bottoms comprising borate esters with the water-wet product alcohol admixture, the bottoms product instead can be simply treated with aqueous mineral acid so as to hydrolyze the borates, precipitate boric acid, and produce an organic phase which then can be separated as described for recovery of product alcohol. However, employment of the water-wet product alcohol cut is convenient, since it affords consumption of water which would otherwise have to be removed from the product by other means.

Treatment of Methanol/Methylheptafluorobutyrate Azeotrope

The methanol/methylheptafluorobutyrate azeotrope described hereinabove can be separated, if desired, from an admixture of the ester and methanol by distilling off the minimum boiling azeotrope to exhaustion of one of the pot components, and recovery of the other as the pure bottoms. The azeotrope can be recovered from a mixture containing a relatively large amount of methanol. Such mixture can be formed, for example, in an esterification reaction of heptafluorobutyric acid and excess methanol. The ester can be removed from the mixture as the azeotrope, leaving a bottoms product comprising methanol and small amounts of other materials such as water. Methanol then can be distilled and recycled to the esterification step.

The method employs fractionation of an admixture of the methanol and methylheptafluorobutyrate to produce an overhead of methanol/methylheptafluorobutyrate azeotrope, which distillation is continued to exhaustion of one of the components, leaving a bottoms product which then will represent a methanol-free ester, or ester-free methanol, depending on the original proportions. Of course, such result can be controlled by addition of one or other to the distillative admixture.

Alternatively, in the above procedure, the overhead of methanol/methylheptafluorobutyrate can be condensed, treated with sufficient water to cause phase separation into a predominantly aqueous/methanol liquid phase, and a heavy predominantly methylheptafluorobutyrate ester-containing liquid phase. The heavy phase can be returned to the distillation step until the methanol content of the original mixture is substantially exhausted. Thus, pure ester can be thus separated and recovered, where desired.

Ordinarily, about 0.1:1 to about 2:1, more usually about 0.1:1 to about 1:1 parts of water per part of condensed azeotrope by weight can be employed. An effective method of treatment of the azeotrope with water to effect separation of the methanol is to equilibrate the condensed azeotrope at a temperature at a range of about −20° C. to 55° C., more usually from about 0° to 30° C. Any suitable pressure can be employed sufficient to maintain substantially liquid conditions. Time of contact with water can be as convenient. This is particularly an advantageous approach to separate and recover methylheptafluorobutyrate from an esterification reaction mixture containing excess methanol. The azeotropic distillation can be carried out to the point in which no appreciable quantity of methanol remains in the distillation pot. The ester then can be subjected to such additional distillation as may be necessary to recover an effectively high purity material.

Treatment of Water/1,1-Dihydroheptafluorobutanol Azeotrope

The binary minimum boiling azeotrope of water/1,1-dihydroheptafluorobutanol is characterized by a boiling point of about 83°–85° C. at substantially atmospheric pressure. This azeotrope is also characterized by a relationship of about 78 weight percent 1,1-dihydroheptafluorobutanol and correspondingly about 22 weight percent water.

This azeotrope can be separated from a mixture of water and 1,1-dihydroheptafluorobutanol by distilling the admixture to exhaustion of one of the pot components. In some instances it can be convenient to add water to a mixture containing the 1,1-dihydroheptafluorobutanol in order to remove the 1,1-dihydroheptafluorobutanol from the mixture at a temperature lower than that of its normal boiling point or at a temperature which can be advantageously more remote from the boiling point of other components which may be in the mixture. If water is added to a mixture containing 1,1-dihydroheptafluorobutanol, sufficient water should be added to accommodate the complete removal of the 1,1-dihydroheptafluorobutanol. This can be compared, of course, from the composition of the azetrope.

Conventional distillation apparatus and procedures are employed in this separation which can be carried out at any convenient pressure both above and below atmospheric pressure. The care and efficiency of the distillation procedure employed depend upon the specific mixtures to be separated and upon the degree of purity desired.

When the azeotropic distillation has proceeded to a point at which one of the azetrope components has been essentially completely distilled from the mixture, the bottoms product, comprising the component in excess in the azeotropic composition, can be recovered as such or distilled to remove it from still other materials in the mixture, as desired. This embodiment is particularly applicable for removing a relatively minor amount of water from a relatively major amount of 1,1-dihydroheptafluorobutanol so that the 1,1-dihydroheptafluorobutanol can then be further distilled and recovered in an essentially water-free state.

This azeotrope is particularly useful for isolating and recovering 1,1-dihydroheptafluorobutanol from a reaction mixture containing substantial amounts of water. Such a mixture is obtained, for example, in a process wherein heptafluorobutyric acid is esterified with methanol, reduced with such as sodium borohydride, treated with aqueous mineral acid, and the resulting admixture flashed. The flashed overhead product comprises 1,1-dihydroheptafluorobutanol, methanol, and water. Upon distillation of the condensed overhead, the first principal overhead product is methanol. After most of the methanol has been removed, a separated water phase can appear in the distillation pot. If desired, the distillation can be temporarily halted and the water phase drawn off.

Ordinarily, as when particularly pure heptafluorobutyric acid is used in the esterification zone, the next major overhead product is the water/1,1-dihydroheptafluorobutanol azeotrope. However, the heptafluorobutyric acid sometimes contains small amounts of pentafluoropropionic acid impurity. This material, if it is present and if it is not removed in an earlier stage can be present now as 1,1-dihydropentafluoropropanol (b. pt. 81° C.). If present, it will go overhead at about 83° C., possibly as an azeotrope with residual methanol.

An efficient method of separating water from a mixture of 1,1-dihydroheptafluorobutanol and water comprises condensing the azeotrope vapor and cooling it under suitable conditions of temperature, time and pressure which are effective to cause a separation of the condensate into two liquid phases. The upper liquid phase consists primarily of water while the lower organic phase consists primarily of ester largely depleted in water content. Only the heavier organic phase is returned to the pot. This is continued until no appreciable amount of phase separation can be obtained from the condensed azeotrope by cooling.

Ordinarily, the condensed azeotrope is cooled to a temperature in the range of from about −20° C. to about 80° C., more usually from about 0° to about 30° C. The pressure can be any convenient pressure which will maintain the liquid phases and the time of cooling will vary, depending upon conditions, and can range from a few seconds to several hours.

The next major fraction is the water/1,1-dihydroheptafluorobutanol which is removed at about 84° C. with return of the cooled heavy phase to the pot. When no further aqueous phase occurs in the cooled condensate and when the head temperature increases, an intermediate "wet product" cut is taken for later recycle and, finally, the essentially pure 1,1-dihydroheptafluorobutanol is taken overhead at about 96° C.

Water/Methyl Heptafluorobutyrate Azeotrope

In the course of my work, I have also discovered a binary minimum boiling water/methyl heptafluorobutyrate azeotrope which is characterized by boiling point of about 68°–70° C. at substantially atmospheric pressure. This azeotrope also can be characterized by a methylheptafluorobutyrate content of about 97 wt. %, and correspondingly about 3 wt. % water, when recovered at substantially atmospheric pressure. This is a minimum boiling azeotrope, since the boiling point of water conventionally is 100° C. at standard pressure, and that of methylheptafluorobutyrate is about 80° C. at standard pressure.

Pure methylheptafluorobutyrate can be recovered, where desired, by distilling an admixture of water and methylheptafluorobutyrate with an excess of methylheptafluorobutyrate, such that the water/methylheptafluorobutyrate is distilled, leaving a pot of substantially pure ester, which subsequently can be fractionated, if desired, to a high purity product.

Where desired, a mixture of water and methylheptafluorobutyrate can be distilled to produce an overhead water/methylheptafluorobutyrate azeotrope. This can be condensed and sufficiently highly cooled to cause phase separation into a light, predominantly aqueous liquid phase and a heavy, predominantly organic liquid phase, and the heavy phase then can be returned to the distillation pot until the water content of the original mixture is substantially exhausted. Temperatures at which the condensate can be cooled can range from about $-20°$ C. to about $75°$ C., more usually about $0°$-$30°$ C., employing any convenient pressure such as atmospheric pressure to maintain substantially liquid phase.

This mode of separation can be particularly useful for separating water from a mixture containing methanol, methylheptafluorobutyrate, water, and possibly minor amounts of materials produced in esterification of such as heptafluorobutyric acid with methanol. Such an admixture can be fractionally distilled, taking overhead the azeotrope of methanol/methylheptafluorobutyrate, thus removing substantially all of the methanol while retaining substantially all of the methylheptafluorobutyrate. Thereafter, a water/methylheptafluorobutyrate azeotrope distills. By employing the method described hereinabove, water can be essentially removed while recovering substantially all of the ester.

Ordinarily, as when particularly pure heptafluorobutyric acid is used in the esterification zone, the next overhead product would be the methylheptafluorobutyrate. However, the heptafluorobutyric acid sometimes contains small amounts of pentafluoropropionic acid impurity. This material, if present, will then go overhead at about $74°$ C. as methyl pentafluoropropionate and possibly as an azeotrope with one or more other components of the system.

Finally, essentially pure methylheptafluorobutyrate comes over at about $80°$-$81°$ C. in a purity generally greater than about 99.5 weight percent.

EXAMPLES

Examples described herein are designed to assist one skilled in the art to which the invention most nearly appertains to a further understanding of the invention, and it is to be understood that particular conditions, components, and the like, are directed to one skilled in the art, are to be considered a portion of my disclosure, not limitative of the reasonable scope thereof.

EXAMPLE I

A 0.506 kg quantity of NaBH$_4$ was charged into a 22-l flask equipped with stirrer and reflux condenser. Into this flask then was pumped 4.75 kg of methanol/methylheptafluorobutyrate azeotrope prepared as described in the run in Example VI. The pumping required about 4.25 hours. External heat was applied to maintain reflux for about one more hour. An acid solution, prepared by adding about 300 g concentrated sulfuric acid to about 900 ml ice, then was pumped into the reaction flask over a period of about 29 minutes.

The reaction flask was then prepared for simple distillation. A distillate principally containing water, 1,1-dihydroperfluorobutanol, and methanol was recovered up to a head temperature of $87°$ C. (atmospheric pressure). A small amount of additional organic material was obtained by adding 2200 ml water to the pot and distilling to a head temperature of about $98°$ C. (atmospheric pressure). The total recovered distillate was about 4.34 kg.

In another substantially similar run, 0.507 kg NaBH$_4$ was reacted with 4.29 kg of the methanol/methylheptafluorobutyrate ester azeotrope to yield 5.13 kg of crude product distillate.

The distillates from these two runs were combined and analyzed. The analysis showed, in weight percent, the presence of 6.5% water, 29.9% methanol, 8.3% ester, 0.5% unknown, and 54.8% 1,1-dihydroperfluorobutanol. Thus, about 5 kg of product alcohol was produced for each kg of NaBH$_4$ used in the reaction.

These runs illustrate the conversion of methylheptafluorobutyrate to 1,1-dihydroperfluorobutanol, and employment of a methanol/methylheptafluorobutyrate azeotrope.

EXAMPLE II

A 22-l flask was charged with 0.191 kg (5.05 moles) of NaBH$_4$ and 2.30 kg (10.1 moles) of undiluted methylheptafluorobutyrate. The flask was equipped with a stirrer and a chilled water condenser. The mixture was heated to reflux, and 0.677 kg (21.16 moles) methanol was slowly pumped in over a period of about 3 hours. The methanol addition resulted in an immediate exothermic reaction and an increase in refluxing rate.

An acid solution, prepared by mixing 500 ml concentrated sulfuric acid in 2-l ice and water, then was pumped into the reaction mixture over a period of about 2 hours, slowly at first, then more rapidly. Another liter of water then was added to the flask together with about 100 ml methanol which was used to rinse the pump.

The reaction flask then was prepared for simple distillation. 3.11 kg of a distillate comprising water, methanol, and 1,1-dihydroheptafluorobutanol was recovered up to a head temperature of about $190°$ F. ($88°$ C.). Analysis of the mixture showed the presence of 1.97 kg of 1,1-dihydroheptafluorobutanol (about 97% of theory). Thus, about 10.3 kg of product alcohol was produced for each kg of NaBH$_4$ used in the reaction.

This run illustrates the conversion of undiluted methylheptafluorobutyrate to 1,1-dihydroheptafluorobutanol.

EXAMPLE III

A 415 g (4.06 moles) quantity of isopropyl acetate was mixed with 39 g (1.03 moles) of NaBH$_4$ and brought to reflux. A 198 g quantity of methanol then was slowly added over a period of about 6 hours. A largely qualitative analysis of a sample of the vapor from the refluxing mixture showed the presence of a substantial amount of ethanol product.

This run illustrates the reduction of a non-fluorinated ester, namely isopropyl acetate, to the corresponding alcohol, ethanol.

EXAMPLE IV

Still another non-fluorinated ester was reduced.

A 295.5 g (3.99 moles) quantity of methyl acetate was mixed with 77.3 g (2.00 moles) NaBH$_4$ and brought to reflux. A 306 g kg quantity of methanol was slowly added to the refluxing mixture over a period of about 6 hours. The mixture was acidified with an acid solution prepared by mixing 300 ml concentrated sulfuric acid in 2-l ice and water. The mixture then was distilled. An analysis of the distillate showed a 66 mole percent conversion of the acetate ester to ethanol.

EXAMPLE V

A 21.3 g (0.563 mole) quantity of $NaBH_4$ was charged to a stirred reaction vessel together with 506.2 g (2.22 moles) of methylheptafluorobutyrate. The mixture was heated to reflux and 125 ml water was added, very slowly at first, then more rapidly, over a period of about 1 hour. A 125 ml quantity of acid, prepared by mixing 200 ml concentrated $H_2SO_4$ in 2-1 ice and water, then was added, and the reaction mixture was subjected to a simple distillation until essentially all of the organic material was distilled. Analysis of the distillate (0.445 kg) indicated the presence of 2 percent water, 2 percent methanol, 47 percent methylheptafluorobutyrate and 49 percent 1,1-dihydroheptafluorobutanol. Thus, about 10.5 kg of 1,1-dihydroheptafluorobutanol was produced per kg of sodium borohydride.

This run illustrates the use of water as a proton source in the $NaBH_4$ reduction of methylheptafluorobutyrate to 1,1-dihydroheptafluorobutanol.

EXAMPLE VI

A 12-1 flask was charged with 6.0 kg heptafluorobutyric acid followed by 3.0 kg methanol. The mixture then was heated, allowed to reflux for about 10 minutes, and then distilled through an Oldershaw column. The methanol/methylheptafluorobutyrate azeotrope was collected at about 56°-58° C. (atmospheric pressure) until about 7.75 kg of the azeotrope was recovered.

This run illustrates the conversion of heptafluorobutyric acid to the methanol/methylheptafluorobutyrate azeotrope.

EXAMPLE VII

About 6 kg of a crude reaction product, the combined flashed overhead from several $NaBH_4$-reductions of methylheptafluorobutyrate in the presence of methanol, was transferred to a 12-l distillation pot. This mixture typically contained about 60 weight percent 1,1-dihydroheptafluorobutanol, about 20 weight percent methanol, about 20 weight percent water, and traces of borate and heptafluorobutyrate esters. The distillation pot was equipped with a 20-tray Oldershaw column. The mixture was distilled to remove the methanol present. The pot contents then were removed, chilled with ice, and a light, largely aqueous layer which formed was removed. The heavy, largely organic phase was returned to the pot for continued distillation. A constant boiling mixture was collected at about 83° C. at atmospheric pressure. Analysis showed it to consist of 22 weight percent water and 78 weight percent 1,1-dihydroperfluorobutanol.

As the azeotrope was removed and cooled, it separated into an aqueous upper layer and a lower organic layer. The organic layer was continuously returned to the pot. Thus, by means of this azeotrope, the heptafluorobutanol conveniently became separated from water. When the water content was reduced to the level of solubility in the product and no further phase separation occurred, an intermediate "wet product cut" was recovered up to about 96° C. Then essentially pure heptafluorobutanol product was distilled and recovered.

This run discloses the composition and boiling point of the water/1,1-dihydroperfluorobutanol azeotrope and illustrates its use in a separation operation.

EXAMPLE VIII

A 2.51 kg quantity of a mixture containing 1.63 kg of heptafluorobutyric acid, the remainder being essentially methylheptafluorobutyrate, was charged to a reaction vessel together with 1.50 kg of methanol and warmed to reflux temperature to esterify the free acid. Another 1.31 kg quantity of 97% methylheptafluorobutyrate and another 1.5 kg quantity of methanol were added to the pot just prior to fractional distillation.

The methanol/methylheptafluorobutyrate azeotrope was fractionally distilled from the mixture at about 134° F. (56.8° C.) at about 749 mm Hg. A 3.90 kg quantity of this azeotrope, containing about 78 weight percent ester, was recovered as overhead product. The pot residue consisted essentially of methanol and water, and was essentially free of methyl heptafluorobutyrate.

This 3.90 kg quantity of azeotropic distillate was analyzed by gas-liquid chromatography and found to contain about 78.1 percent ester, 21.3 percent methanol, and about 0.5 percent water, by weight. It was then mixed with 800 ml of water, allowed to settle into two liquid phases, and the heavier organic phase was drawn off. The treatment with 800 ml water was repeated leaving 2.96 kg of water-wet but largely methanol-free methylheptafluorobutyrate which was suitable for return to the fractional distillation separation process for further purification.

This run illustrates the methanol/methyl heptafluorobutyrate and its use in separation operations.

EXAMPLE IX

A 4.21 kg quantity of water-wet methylheptafluorobutyrate was charged to a distillation flask. After the mixture began refluxing, an additional 10 ml water was added. The mixture was subjected to fractional distillation. A constant boiling mixture was collected at an overhead temperature of about 69° C. (74.5 mm). This azeotrope was found to contain about 3.0 weight percent water.

As the azeotrope was condensed and cooled, it separated into two liquid phases, the upper phase being essentially water and the lower phase being essentially ester. The upper aqueous phase was discarded and the lower ester phase was intermittently returned to the distillation vessel. Eventually the head temperature rose to about 80° C. and 2.84 kg of methylheptafluorobutyrate was recovered. Analysis by gas-liquid chromatography showed no detectable water in the ester.

This run discloses the composition and boiling point of the water/methylheptafluorobutyrate azeotrope and illustrates its use in a separation operation.

EXAMPLE X

The pot end remaining after the distillation of four batches of crude 1,1-dihydroheptafluorobutanol, such as prepared in Example I, and containing 1,1-dihydroheptafluorobutyl borate salts, was contacted with the "wet 1,1-dihydroperfluorobutanol cut" obtained from a previous product distillation and recovery. This "wet cut" was the fraction which followed the point (about 83° C.) at which azeotropic water could be separated from the distillate as a separate phase (see Example VII) up to the product take-off temperature of about 96° C. The "wet cut" and pot ends were mixed at room temperature, allowed to stand for several hours then filtered to remove solid boric acid.

The filtrate, now depleted in water and enriched in 1,1-dihydroheptafluorobutanol, was charged to the distillation pot of another fractional distillation run at the point at which most of the methanol was distilled off and the water layer in the pot was removed. The fractional distillation process then was continued, as in Example VII, to produce a pure 1,1-dihydroheptafluorobutanol fraction as well as another "wet cut" and another residue of pot ends.

This example illustrates the recovery of heptafluorobutyl values from the residual heel of a 1,1-dihydroheptafluorobutanol fractional distillation run.

EXAMPLE XI

An 1800 g quantity of methanol (b. pt. 65° C.) was charged to a 5-l flask together with 1750 g of heptafluorobutyric acid (b. pt. 80° C.) which was washed in with another 100 ml methanol. These reactants were allowed to stand over the weekend at room temperature. About one-half of this mixture was transferred to a 3-l distillation pot containing some quartz chips and equipped with a 5-section Snyder column and a water condenser.

The mixture was distilled. A constant boiling mixture was collected at an overhead temperature of 57° C. at atmospheric pressure. After collecting about 654 g of distillate, the remaining half of the original mixture was added to the pot and additional distillate was collected at a head temperature of 57° C. until a total of about 1531 g was collected. Analysis of this distillate showed it to be a mixture of about 20 weight percent methanol and 80 weight percent methyl heptafluorobutyrate. Similar distillation of the constant boiling mixture from an ester-rich mixture also exhibited essentially the same boiling point and composition.

This run illustrates the composition and boiling point of the methanol/methylheptafluorobutyrate azeotrope.

Constant boiling admixtures are liquid mixtures of two or more substances which mixtures behave like a single substance in that the vapor produced by partial evaporation or distillation has the same composition as does the liquid, i.e., the admixtures distill without change in composition. Constant boiling compositions characterized as azeotropes exhibit either a maximum or minimum boiling point as compared with that of nonazeotropic mixtures of the same substances. It is not possible to predict what two or more substances will combine to form azeotropes as the resultant mixture must exhibit nonideal phase behavior in order for an azeotrope to form, and non-ideal phase behavior is unpredictable.

Of course, the weight percentage relationship can be subject to some variation depending upon the particular atmospheric pressure encountered upon distillation, since the relationship of the azeotropic components depends to a great extent upon the temperature of distillation which depends, of course, correspondingly on the atmospheric pressure involved.

At differing pressures, the composition of a given azeotrope will vary, at least slightly, and changes in distillation pressures also change, at least slightly, the distillation temperatures. Thus, an azeotrope of A and B represents a unique type of relationship but with a variable composition depending upon temperature and/or pressure.

It is possible to fingerprint, in effect, a constant boiling admixture, which may appear under varying guises depending on the conditions chosen, by any of several criteria: The composition can be defined as an azeotrope of A and B, since the very term "azeotrope" is at once both definitive and limitative, requiring that A and B indeed form this unique composition of matter which is a constant boiling admixture. Or, the composition can be defined as a particular weight percent relationship or mole percent relationship of A:B, while recognizing that such specific values point out only one particular such relationship and that in actuality a series of such relationships represented by A:B actually exist for a given azeotrope, varied by influence of distillative conditions, the temperature and pressure relationship. Or, recognizing that the azeotrope A:B does represent just such a series of relationships, the azeotropic series represented by A:B can be characterized by defining the composition as an azeotrope characterized by a boiling point at a given pressure, thus given identifying characteristics without unduly limiting the scope of the invention by a specific numerical composition, which is limited by and is only as accurate as the analytical equipment available.

The disclosure, including data, illustrate the value and effectiveness of my invention. The examples, the knowledge and background of the field of the invention, and general principles of chemistry and other applicable sciences, have formed the bases from which the broad descriptions of the invention including the ranges of conditions and generic groups of operant components have been developed, which have formed the bases for my claims here appended.

I claim:

1. A substantially constant boiling admixture of methanol and methyl heptafluorobutyrate characterized by a boiling point of about 56°–58° C. at substantially atmospheric pressure.

2. The composition according to claim 1 characterized by a methyl heptafluorobutyrate content of about 78–80 weight percent, and a methanol content of about 22–20 weight percent.

3. The composition according to claim 1 characterized as a minimum boiling azeotrope.

4. A process of separating an admixture comprising methanol and methyl heptafluorobutyrate which comprises the steps of:
   (a) distilling a mixture comprising methanol and methyl heptafluorobutyrate to produce an overhead methanol/methyl heptafluorobutyrate azeotrope,
   (b) condensing said overhead,
   (c) adding water to the condensed overhead, thereby effecting a phase separation into a predominantly aqueous methanol liquid phase and a predominantly ester-containing liquid phase,
   (d) separating said phases,
   (e) returning the predominantly ester-containing liquid phase to said distillation step until the methanol content in said admixture is substantially exhausted, thereby obtaining a substantially pure methyl heptafluorobutyrate.

5. The process according to claim 4 employing about 0.01:1 to about 2:1 parts of water per part of condensed azeotrope and employing a temperature in the range of about −20° C. to 55° C. in said step (c) and a pressure sufficient to maintain substantially liquid phase conditions.

* * * * *